US012805947B2

(12) United States Patent
DeBuys et al.

(10) Patent No.: US 12,805,947 B2
(45) Date of Patent: Nov. 24, 2026

(54) SEPARABLE ROBOTIC CATHETER MECHANISM

(71) Applicant: Siemens Medical Solutions USA, Inc., Malvern, PA (US)

(72) Inventors: Christian DeBuys, Metairie, LA (US); Young-Ho Kim, West Windsor, NJ (US); Tommaso Mansi, Plainsboro, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 340 days.

(21) Appl. No.: 18/576,240

(22) PCT Filed: Aug. 9, 2022

(86) PCT No.: PCT/US2022/074689

§ 371 (c)(1), (2) Date: Jan. 3, 2024

(87) PCT Pub. No.: WO2023/019123

PCT Pub. Date: Feb. 16, 2023

(65) Prior Publication Data

US 2024/0307133 A1 Sep. 19, 2024

Related U.S. Application Data

(60) Provisional application No. 63/231,875, filed on Aug. 11, 2021.

(51) Int. Cl.
*A61B 34/30* (2016.01)
*A61B 17/00* (2006.01)

(52) U.S. Cl.
CPC .............. *A61B 34/30* (2016.02); *A61B 17/00* (2013.01); *A61B 2017/00398* (2013.01); *A61B 2017/0046* (2013.01); *A61B 2034/301* (2016.02)

(58) Field of Classification Search
CPC ... A61B 34/30; A61B 17/00; A61B 2034/301; A61B 2017/00398; A61B 2017/0046
See application file for complete search history.

(56) References Cited

U.S. PATENT DOCUMENTS

| | | | | |
|---|---|---|---|---|
| 11,730,349 B2 * | 8/2023 | Altshuler | .......... | A61B 1/00121 600/114 |
| 12,076,505 B2 * | 9/2024 | Haubert | ............ | A61M 25/0097 |

(Continued)

FOREIGN PATENT DOCUMENTS

| | | |
|---|---|---|
| CN | 110977935 A | 4/2020 |
| EP | 0513224 B1 | 10/1996 |

(Continued)

OTHER PUBLICATIONS

Kim, Young-Ho, and Tommaso Mansi. "Shape-adaptive Hysteresis Compensation for Tendon-driven Continuum Manipulators." arXiv preprint arXiv:2109.06907 (2021).

(Continued)

*Primary Examiner* — Shirley X Jian

(57) ABSTRACT

In a robotic or even manually controlled catheter, more direct connection of the force application (e.g., actuators) is provided from the handle to the tendons. The actuators are part of the handle. To avoid discarding the actuators after each use, the handle with the actuators is separable from a (Continued)

housing for the tendons. The housing for the tendons includes a clamp to hold the tendons in place prior to connecting with the handle and actuators.

17 Claims, 4 Drawing Sheets

(56) References Cited

U.S. PATENT DOCUMENTS

| | | | |
|---|---|---|---|
| 2007/0287909 | A1 | 12/2007 | Garibaldi et al. |
| 2014/0107661 | A1 | 4/2014 | Viswanathan et al. |
| 2019/0274699 | A1 | 9/2019 | Morey et al. |
| 2020/0060646 | A1 | 2/2020 | Lindenroth et al. |
| 2020/0078559 | A1 | 3/2020 | Guo et al. |
| 2021/0022816 | A1 | 1/2021 | Debuys et al. |
| 2021/0023337 | A1 | 1/2021 | Debuys et al. |
| 2021/0145522 | A1 | 5/2021 | Debuys et al. |
| 2022/0040450 | A1 | 2/2022 | Haubert |

FOREIGN PATENT DOCUMENTS

| | | | |
|---|---|---|---|
| EP | 3175812 | A1 | 6/2017 |
| JP | 2007029274 | A | 2/2007 |
| WO | 2017136710 | A2 | 8/2017 |
| WO | 2019133439 | A1 | 7/2019 |

OTHER PUBLICATIONS

Kim, Young-Ho, et al. "Automated catheter tip repositioning for intra-cardiac echocardiography." International Journal of Computer Assisted Radiology and Surgery (2022): 1-9.

Lee, Dong-Ho, et al. "Non-linear hysteresis compensation of a tendon-sheath-driven robotic manipulator using motor current." IEEE Robotics and Automation Letters 6.2 (2021): 1224-1231.

Li Zhongyu, et al. "Zero-fluoroscopy transseptal puncture guided by intelligent intracardiac echocardiography robotics." Journal of the American College of Cardiology 77.18_Supplement_1 (2021): 970-970.

Loschak, Paul M., et al. "A 4-DOF robot for positioning ultrasound imaging catheters." International Design Engineering Technical Conferences and Computers and Information in Engineering Conference. vol. 57120. American Society of Mechanical Engineers, 2015.

Sterotaxis Products—Vdrive. pp. 1-6. Obtained Jul. 21, 2022. https://www.stereotaxis.com/.

International Search Report mailed Mar. 9, 2023 in corresponding International Patent Application No. PCT/US2022/074689.

Debuys, Christian, et al.; "Design and validation of zero-slack separabe manipulator for Intracardiac Echocardiography", arxiv.org, Cornell University Library, 201 Olin Library Cornell University Ithaca, NY 14853, Apr. 1, 2022, the whole document.

* cited by examiner

FIG. 1
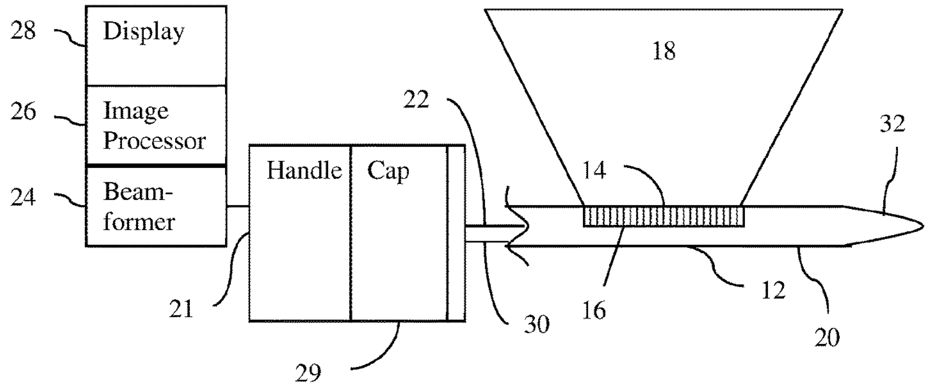
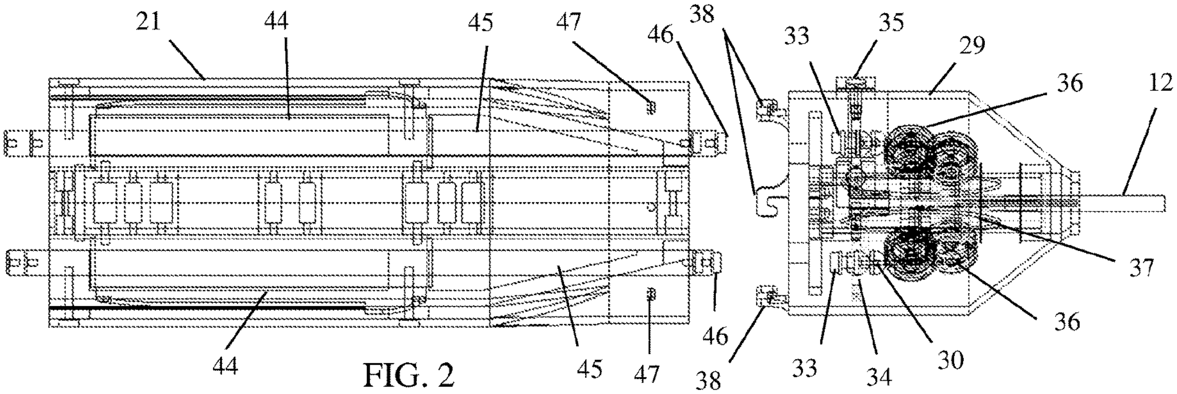
FIG. 2
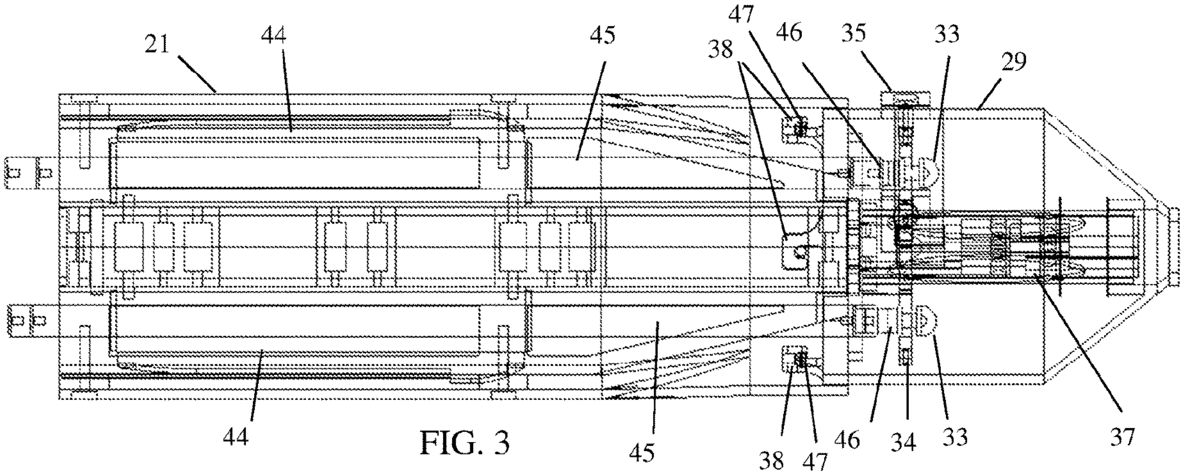
FIG. 3

SEPARABLE ROBOTIC CATHETER MECHANISM

RELATED APPLICATION

The present patent document claims the benefit of the filing date under 35 U.S.C. § 119(e) of Provisional U.S. Patent Application Ser. No. 63/231,875, filed Aug. 11, 2021, and is a national phase filing under 35 U.S.C. § 371 of International Patent Application No. PCT/US2022/074689, filed Aug. 9, 2022, which is are incorporated herein by reference in their its entirety.

FEDERALLY SPONSORED RESEARCH OR DEVELOPMENT

This invention was made with government support under grant no. 5-R01-EB028278-03 awarded by the NIH. The government has certain rights to this invention.

BACKGROUND

The present embodiments relate to robotic control of a medical catheter. One example medical catheter is an intracardiac echocardiography (ICE) catheter, which is used for cardiac interventional and diagnostic procedures. ICE can provide close feedback of anatomical structures and tools during a surgical procedure. One major challenge ICE and other interventional catheterization poses for the operating interventionalist is the difficult catheter manipulability.

Robotic control systems may aid manipulability. A commercially available robotic system for ultrasound catheter manipulation is the Stereotaxis Vdrive system. The motorized system is in a base, and there exist multiple gearing structures, combined to the outer knobs of catheter. A tendon-sheath mechanism (TSM) generally consists of a long and flexible hollow coil pipe acting as a sheath, and a wire that in inserted into the coil pipe and acts as the tendon. When the wire is pulled at one end, it slides within the sheath so that the pulling force is transmitted to the other end of the sheath. For motorized TSM-based catheter systems, the actuators interface with the knobs of an existing catheter. There are many layers to this interface, leading to slack and difficulty in precise control. Thus, there exist significant slack, so it is challenging to transfer instant torques from motors to tendons.

SUMMARY

By way of introduction, the preferred embodiments described below include methods, systems, and robots for operating a catheter. In a robotic or even manually controlled catheter, more direct connection of the force application (e.g., actuators) is provided from the handle to the tendons. The actuators are part of the handle. To avoid discarding the actuators after each use, the handle with the actuators is separable from a housing for the tendons. The housing for the tendons includes a clamp to hold the tendons in place prior to connecting with the handle and actuators.

In a first aspect, a robotic catheter system is provided. A handle includes one or more actuators. A housing cap is releasably connectable with the handle. The housing cap has one or more tendons connected to a catheter. The handle and housing cap are configured so that, when the housing cap connects with the handle, the one or more tendons engage with the one or more actuators.

In one embodiment, the one or more actuators are one or more linear actuators.

In another embodiment, the one or more tendons terminate at respective one or more anchors where the one or more anchors are releasably connectable to shafts of the one or more actuators, respectively. For example, the anchors or ends of shafts are magnets such that the anchors are releasably connectable to the ends of the shafts via magnetism.

According to another embodiment, the housing cap has one or more extensions configured to connect to the handle with a twist motion. For example, the housing cap has a spring configured to be compressed for connection of the housing cap with the handle. The extensions include hooks to engage the handle where the spring disposes the hooks to stay in place when connected.

In one embodiment, the housing cap has a releasable clamp configured to hold the one or more tendons when the housing cap is not connected to the handle. For example, the one or more tendons terminate at one or more anchors, respectively. The releasable clamp is configured to hold the one or more anchors until the housing cap connects to the handle. As another example, the releasable clamp is a fan lock connected to a slider exposed on an exterior of the housing cap. The fan lock is configured to release the one or more tendons in response to movement of the slider relative to the housing cap.

In a second aspect, a method is provided for separating a catheter from a robotic component. One or more actuators are housed in a handle. One or more tendons terminate in a cap. The cap is releasably connected to the handle. Releasably connecting the cap to the handle connects one or more shafts of the one or more actuators to the one or more tendons, respectively.

As one embodiment, releasably connecting includes pressing the cap to the handle and against a spring force and twisting the cap relative to the handle, the twisting engaging the cap to the handle.

In another embodiment, terminal ends of the one or more tendons are clamped in the cap, and the clamping is released after the cap is releasably connected to the handle.

In a third aspect, a catheter system is provided. A housing connects with a catheter. One or more tendons of the catheter extend into the housing. A releasable clamp in the housing is configured to clamp the one or more tendons.

In one embodiment, the one or more tendons terminate at one or more anchors, respectively. The releasable clamp is configured to clamp the one or more anchors. For example, the one or more anchors are one or more bushings, respectively. The releasable clamp is configured to clamp around a part of each of the one or more bushings.

As another embodiment, the releasable clamp is configured to clamp all the one or more tendons.

In another embodiment, the releasable clamp is a fan lock. For example, the fan lock is two plates with at least one of the plates rotatable in relative to another of the plates where rotation in a first direction clamps terminal ends of the one or more tendons and where rotation in a second direction releases the terminal ends.

According to an embodiment, a slider on an exterior of the housing connects to the releasable clamp to release the one or more tendons.

In yet another embodiment, a handle is releasably connectable with the housing where the handle being connected with the housing also connects shafts of actuators in the handle with the one or more tendons. The releasable clamp is configured to clamp until the one or more tendons are connected to the shafts.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a medical ultrasound system for imaging with an ICE catheter;

FIG. 2 illustrates one embodiment of a robotic catheter system with the handle and housing cap separated;

FIG. 3 illustrates another embodiment of a robotic catheter system with the handle and housing cap connected;

DETAILED DESCRIPTION OF THE DRAWINGS AND PRESENTLY PREFERRED EMBODIMENTS

Figure 4:
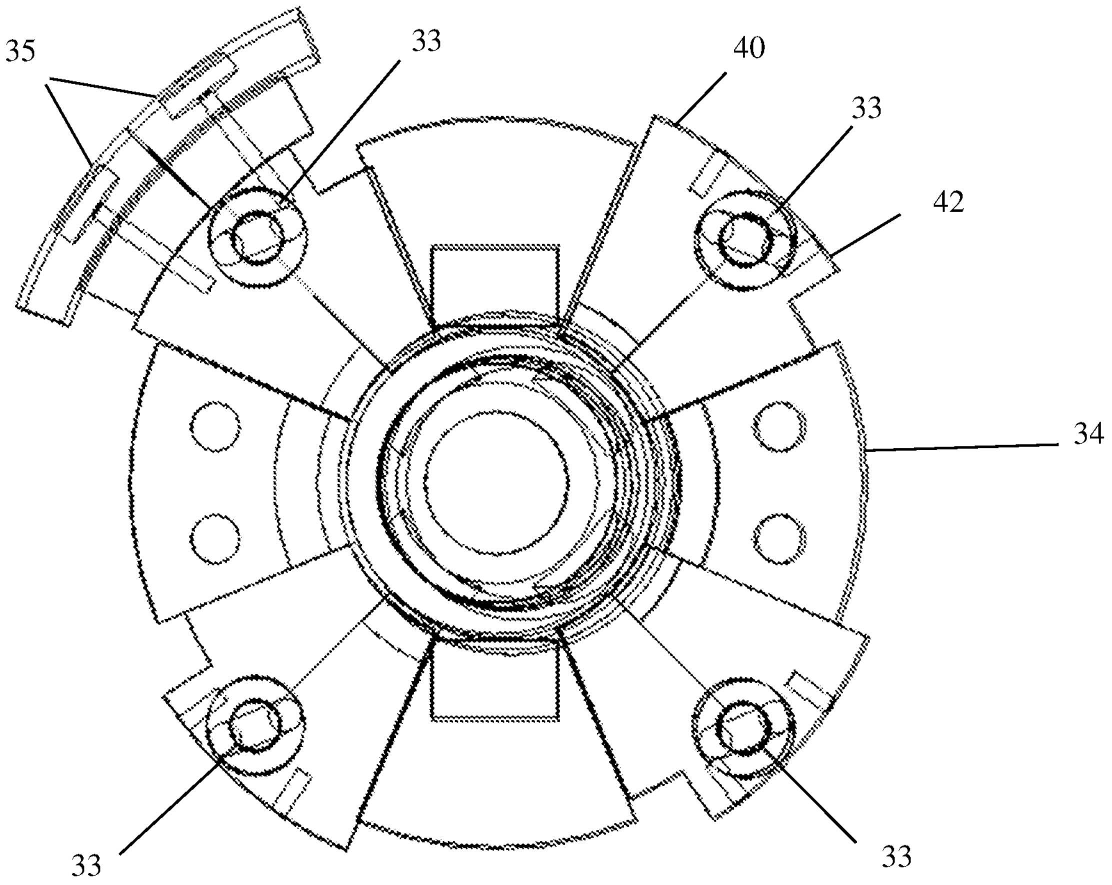
FIGS. 4 and 5 are top views of a fan lock in clamped and open positions, respectively, according to one embodiment.

Actuators are inside the catheter handle, permitting direct interfacing between the actuators and the tendons. Once the actuators are included in the handle, it is no longer feasible for the catheter to be disposable without unnecessary cost. A distal portion of the catheter is separable from a handle. The handle of the catheter, with the included electronics, is reusable. Cleaning the electronic components may be avoided with the electronics in the handle.

To provide for a reusable handle, a clipping system keeps the handle sterile and reusable. A front part connected with the catheter is disposable. The tendons are held in place in the front part. When the front part is clipped to the handle, the tendons are attached to the actuators by fasteners. The clipping system facilitates the easy attachment and detachment of the distal portion from the handle. In this way, the handle of the catheter, including the electronic components, is reusable, and the distal portion is disposable.

The front part holds the tendons in place until the system is clipped. For example, the tendons attach to tendon anchors, and a fan lock holds the anchors in place. After the system is clipped, two sliders are pushed apart to open the fan lock and allow motion of the tendons.

FIG. 1 shows an example medical ultrasound system for ICE. The examples herein are in the context of robotic control of an ICE catheter. In other examples, other types of catheters for insertion within a cardiac system of a patient, such as ablation or stenting catheters, use the separable handle and/or tendon clamping. In another example, the separable handle and/or tendon clamping are provided for manually operated catheters (i.e., catheters without motors) rather than robotic controlled catheters.

FIG. 1 is directed to the catheter ICE embodiment. FIGS. 2-6 are directed to separable handle and/or tendon clamping. FIG. 1 is described below first to provide the context for the example catheter usage.

The example medical ultrasound system of FIG. 1 uses the ICE catheter 12, which may be robotically controlled. The medical ultrasound system includes the ICE catheter 12, a beamformer 24, an image processor 26, and a display 28. Additional, different, or fewer components may be provided, such as providing just the catheter 12. The catheter 12 releasably connects with the imaging system.

The ICE catheter 12 includes an array 14 of elements 16 for imaging within a shaft or housing 20 having a tip 32, electrical conductors 22, steering wires (tendons) 30, and a handle 21. Additional, different, or fewer components may be provided, such as radio opaque markers, ablation electrodes, lens, needle guide, or ports. In other embodiments, the catheter 12 is an ablation catheter or interventional catheter rather than an imaging catheter.

The shaft housing 20 is PEBAX, nylon, polymer, or other flexible material. The shaft housing 20 is formed around the array 14 and other parts extending from the handle 21 and insertable into the patient. The shaft housing 20 is configured for insertion into a circulatory system of a patient. For example, the distal tip 32 of the catheter 12 includes a more flexible portion covered by the shaft housing 20 for moving through the circulatory system. Tendons 30 connected to the shaft housing 20 or parts (e.g., anchor points) within the housing 20 are configured to guide the shaft housing 20 within the circulatory system.

The array 14 is positioned within the catheter 12. The array 14 may fit within 10 French, 3.33 mm, 12.5 French, or another diameter catheter 12. The array 14 is at a distal end or tip 32 of the catheter 12, such as being within 20 mm of an end of the tip 32 or a beginning of a flexible tip portion. The array 14 may have any position within the catheter 12 that results in the array 14 being within the patient during use of the catheter 12 for imaging.

The transducer array 14 is used for ultrasound imaging. The images assist in diagnosis, catheter guidance, needle guidance, ablation guidance, placement, and/or needle puncture. The array 14 scans in a field of view 18 in a plane perpendicular to the emitting face. The patient within the field of view 18 may be imaged using the array 14.

Electrical conductors 22 connect the elements 16 of the array 14 to the beamformer 24. The conductors 22 are cables, coaxial cables, traces on flexible circuit material, wires, wire jumpers, combinations thereof, and/or other now known or later developed conductor.

The beamformer 24 includes a plurality of channels for generating transmit waveforms and/or receiving signals. Relative delays and/or apodization focus the transmit waveforms or received signals for forming beams and setting a focal location. The beamformer 24 connects with the conductors 22 for applying waveforms for imaging with the array 14 and receiving signals. For imaging, the beamformer 24 selects an aperture including one, some, or all of the elements 16 of the array 14. For scanning, the beamformer 24 electronically focuses along the azimuth direction. A plurality of scan lines using an aperture is scanned. During receive operations, the focus may vary as a function of depth (i.e., dynamic focusing).

The image processor 26 is a detector, filter, processor, application specific integrated circuit, field programmable gate array, digital signal processor, control processor, scan converter, three-dimensional image processor, graphics processing unit, analog circuit, digital circuit, or combinations thereof. The image processor 26 receives beamformed data and generates images on the display 28, which is a display screen.

The tendons (steering wires) 30 of the catheter 12 are used to position the array 14 (and/or medical instrument) relative to the patient. The tendons 30 are cables, wires, or other structure for transferring push and pull force from the handle 21 to a portion of the catheter 12 within a patient, such as to the distal end or the tip 32. Any material may be used, such as plastic, fiberglass, or metal. Any number of tendons 30 may be used, such as three or four wires. For example, three or four tendons 30 offset from the center in an equal spacing about the center or longitudinal axis may be used to steer along two perpendicular planes. The tendons 30 run through the elastic material of the catheter body or shaft housing 20 to the distal end and are arranged in a circular fashion around a central channel, which provides sufficient space for the ultrasound transducer cable or conductors 22 to be guided through. The relative force between the tendons 30 causes the catheter 12 to bend. Any now known or later developed arrangement of tendons 30 may be used.

The tendons 30 control the bend at a distal end of the catheter 12. The bend may be at a portion of the catheter 12 adjacent to the distal end or tip 32, such as providing for the array 14 to be spaced from the handle 21 by the bend. For example, the tendons 30 are anchored to the shaft housing 20, transducer array 14, or a rigid insert or anchor near the distal end to cause the bend. The elastic body or shaft housing 20 may be bent along its principal axes by applying tension to the attached tendons 30. Using motors instead of user-based rotation of two knobs for two planes allows for only three tendons 30 for forming the bend. Four tendons 30 with motor-based control may be used.

The handle 21 and cap 29 form a housing kept external to the patient. The housing is held by the user, clamp, or robot. The housing connects to the catheter 12 for steering and operating the catheter 12. The housing is separated into two parts, the handle 21 and cap 29.

The handle 21 includes a housing with or without user input in the form of one or more knobs, sliders, or buttons. The handle 21 is shaped and sized for handheld guidance or use of the catheter 12. For example, the handle 21 is cylindrical with grips to be used by one hand of a surgeon. The handle 21 has a single housing made of one or more parts connected with a cable or cables for power and communication. A processor for control may be included in the handle 21 or be external to the handle 21.

The cap 29 includes a housing connected with the shaft housing 20 of the catheter 12. The cap 29 is sized and shaped for connection with the handle 21.

FIG. 2 shows the handle 21 and cap 29 separated, such as prior to use for imaging a patient with the ICE catheter 12. The catheter system may be used for manual powering of steering or for robotic powering of steering. For robotic power, one or more buttons are provided for controlling actuators 44. For manual power, knobs are provided instead of the actuators 44.

Each of the parts (handle 21 and cap 29) has a housing. The housings are plastic, fiberglass, metal, resin, silicone, and/or another material. The shafts, gearing, spools, and/or other components are plastic, metal, or another material.

The handle 21 includes one or more actuators 44. For example, two, three, or four actuators 44 are provided, evenly spaced around a longitudinal center of the handle 21. The actuators 44 are within the handle 21, such as interior to the outer housing, but may be on an outer surface of the handle 21. Additional, different, or fewer components may be provided in the handle 21, such as including a controller or processor for operating the actuators 44 and/or buttons for controlling the actuators 44.

The actuators 44 are motors, such as servo motors, rotational motors, linear motors (e.g., linear magnetic motors), or other electric, pneumatic, or hydraulic motors for moving the shafts 45. In one embodiment, the actuators 44 are linear motors for moving the shafts 45 along a longitudinal dimension (e.g., extending and retracting the shafts 45 relative to the actuators 44). Alternatively, gearing or transmission is provided to convert rotational motion of the shafts 45 to pulling or pushing along the longitudinal direction.

The shafts 45 include a magnet 46 at the end. The magnets 46 are glued or fused to the end of the shafts 45. The connection is fixed. Alternatively, the shaft 45 itself is formed from magnetic material. In other embodiments, the magnets 46 fixedly connect to the tendons 30 or anchors 33 of the tendons 30. In alternatives, other devices than magnets are used, such as having a flexible (e.g., plastic) clip, such as an extension with a ball or protrusions that snap fits with an accepting female part on the shafts 45 and tendons 30 or anchors 33.

The cap 29 is a housing. The cap 29 connects with the catheter 12. The connection may be fixed, such via bonding or formation as a uniform body.

The cap 29 includes terminal or end parts of the tendons 30, anchors 33 for the tendons 30, a clamp 34, one or more sliders 35, one or more spools 36, a spring 37, and one or more extensions 38. Additional, different, or fewer components may be provided. For example, the spools 36 are not provided (see FIG. 3 for the cap 29 without spools 36). As another example, the spring 37, sliders 35, clamp 34, and/or anchors 33 are not provided. In another example, the extensions 38 are on the handle 21 rather than the cap 29.

The cap 29 is sized and shaped for releasable connection with the handle 31. For example, an outer circumference of the cap 29 at an end for mating with the handle 21 is sized to fit over the handle 21, fit within the handle 21, or abut against (same size) as the handle 21. In the embodiment shown in FIGS. 2 and 3, the end of the cap 29 fits snuggly within an opening or indentation of the handle 21.

Any releasable connection may be used. For example, a press fit is used. In another example, threading is provided on the cap 29 and the handle 21 for mating together. A snap fit or other male-female connection may be provided. In the example embodiment of FIGS. 2 and 3, the extensions 38 mate with structure 47 of the handle 21. The extensions 38 are configured to connect with the structure 47 of the handle 21 for releasable connection. In one embodiment, the extensions 38 are hooks for mating with prongs as the structure 47. The cap 29 is pressed against the handle 21 and then twisted to connect with the handle 21 such that the hooks engage the prongs as shown in FIG. 3. The spring 37 may push the cap 29 away from the handle 21. When the extensions 38 engage the structure 47 after pressing and twisting, the spring 37 maintains a force to keep the structure 47 engaged against the extensions 38. Other releasable clamping arrangements may be used, such as provided for child safety medicine bottles.

The cap 29 is connected to the handle 21 for use in surgery. Once complete, the cap 29 may be disconnected from the handle 21, such as by twisting, pulling, pushing, or combination thereof (e.g., push, twist, and then pull apart). Compared to throwing the whole catheter away or cleaning the catheter (including electronic components) after each use, the handle 21 with the more expensive electronics (e.g., actuators 44) is kept while the catheter 12 and connected cap 29 are thrown away after one use. The handle 21 may be reused with another cap 29 and catheter 12. The new cap 29 is releasably connected to the handle 21 for this subsequent use. The handle 21 may be reused without cleaning or is cleaned for reuse.

The tendons 30 terminate in the cap 29. The tendons 30 extend from the catheter 12 into the cap 29. The plastic, metal, or other material spools 36 may route (e.g., reel and align) the tendons 30 to the ends of the shafts 45. Other guide structures than spools 36 may be used, such as posts or grooves.

The ends of the tendons 30 are in the cap 29. Other parts, including a greater length, of the tendons 30 extend from the cap 29 within the catheter 12. The ends of the tendons 30 in the cap 29 may be bare wire. In other embodiments, an anchor 33 connects to each of the tendons 30. The anchor 33 is a terminal end of the tendon 30. The anchor 33 may have any shape, such as being a rod or plate where the tendon 30 connects to a cross bar. In the embodiment shown in FIGS. 2-5, the anchors 33 are bushings with an attached arc bar. The tendons 30 tie off on or are connected to the arc bar.

The handle 21 and the housing cap 29 are configured so that when the housing cap 29 connects with the handle 21, the tendons 30 engage with the actuators 44. The tendons 30, as aligned by the cap 29, terminate at a spatial position so that the ends of the shaft 45 contact the tendons 30 when the cap 29 connects with the handle 21. For example, the pushing and twisting to engage the extensions 38 with the handle structures 47 connects the cap 29 to the handle 21 as shown in FIG. 3. As connected, the ends of the shafts 45 are positioned against or next to the anchors 33 as the ends of the tendons 30.

The ends of the tendons 30 mate with or releasably connect with the ends of the shafts 45. For example, the anchors 33 connect to the ends of the shafts 45. The connection may be by snap fit or other male-female connection. In the embodiment shown, the anchors 33 are ferrous metal. The magnets 46 formed at or bonded to the shafts 45 magnetically connect to the anchors 33, holding the anchors 33 to the shafts 45. This forms a releasable connection where lower forces do not disconnect but a larger force will disconnect. Magnetism, snap fit, or another arrangement is used to releasably connect the shafts 45 to the tendons 30 when the cap 29 is connected to the handle 21. When the front part (housing cap 29) is clipped to the handle 21 as shown in FIG. 3, the tendons 30 are attached to the actuators 44 by fasteners of some type (e.g., magnet to ferrous metal).

This fastening provides a direct connectivity between motorized system (i.e., actuators 44) and tendons 30. The direct connection without intervening gears increases accuracy of tip controls. By having a releasable connection, the separable structure may reduce a total cost of the catheter since the permanent devices (e.g., motor, motor drivers) and disposable devices (e.g., a long tail and threads) are separable. The handle 21, including the actuators 44 via the shafts 45 are releasably connectable with the cap 29. The handle 21 being connected with the housing (cap 29) also connects shafts 45 of actuators 44 in the handle 21 with the one or more tendons 30.

The clamp 34 clamps the tendons 30. The clamp 34 may clamp the tendons 30 spaced from the end or at the end of the tendons 30. For example, the clamp 34 clamps the anchors 33. One clamp 34 may clamp all of the tendons 30, or different clamps 34 clamp different tendons 30. Multiple tendons 30 may be locked and released together. The locking and releasing mechanism of the clamp 34 facilitates assembly of a motorized part and a catheter tail.

The clamp 34 is releasable. The clamp 34 may release the tendons 30. For example, the clamp 34 clamps the tendons 30 until the shafts 45 connect with the tendons 30. The clamp 34 may release upon connection of the tendons 30 with the actuators 44 or some period after this connection. The releasable clamp 34 of the housing cap 29 is configured to hold the tendons 30 when the housing cap 29 is not connected to the handle 21. The clamp 34 holds the tendons 30 during and/or after manufacture of the cap 29 until the tendons 30 connect with the actuators 44 of a handle 21 for use with a patient. The clamp 34 holds the tendons 30 in place until the system is clipped together (handle 21 mates with the cap 29). More specifically, the tendons 30 are attached to tendon anchors 33, and the anchors 33 are held in place by the clamp 34. After use, the clamp 34 may not re-clamp when the handle 21 is disconnected from the cap 29 as the cap 29 and tendons 30 are to be thrown away.

Figure 5:
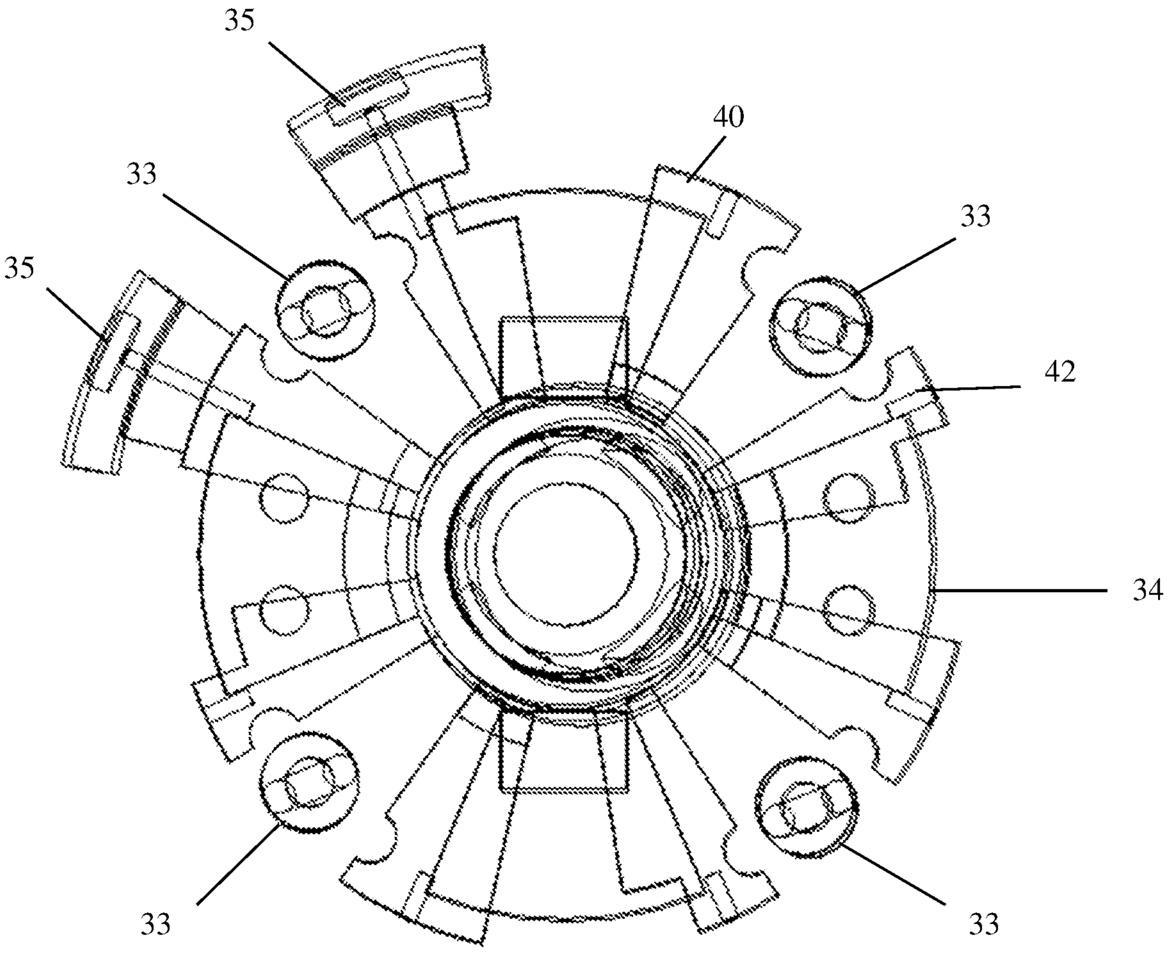

Various clamps 34 may be used. For example, a lever arm presses a pad against the tendon 30, clamping the tendon 30 between the pad and another pad or a plate. As another example, an extension presses into or against the tendon 30. In yet another example, a retractable prong extends through or into a hole in the anchor 33. In one embodiment, a fan lock is used. FIGS. 4 and 5 show an example fan lock. The fan lock includes a plate 40 rotatable relative to another plate 42 or support. Both plates 40, 42 may rotate, such as rotating different directions about a same center axis. FIG. 4 shows the fan lock where one or both of the plates 40, 42 rotate to close around the anchors 33, such as fitting within the bushings of the anchors 33 so that the anchors 33 cannot move, at least more than a few mm, into or out of the page. The clamp 34 clamps to a part of each anchor 33 (e.g., to a narrower part of the bushings). To release, one or both plates 40, 42 are rotated so that the anchors 33 are no longer held. FIG. 5 shows an example. Upon release, the anchors 33 and corresponding tendons 30 may move into or out of the page of the drawings (i.e., along the longitudinal direction of the catheter 12, handle 21, and/or the shafts 45). Rotation in one direction causes clamping, and rotation in an opposite direction releases the clamping (i.e., releases the tendons 30).

Any release mechanism may be used. In one embodiment, a prong or other mechanism releases the clamp 34 as the handle 21 is connected to the cap 29. For example, a spring pre-disposes the clamp 34 in a closed position. Upon pressing the handle 21 to the cap 29, force from the handle 21 overcomes the spring, releasing the clamp 34. In another embodiment, movement of one or more actuators 44 causes release of the clamp 34. The force applied by the actuators 44 snaps or overcomes the clamp force, releasing the tendons 30. In yet another embodiment, one or more sliders 35 are provided for manual release by a user. The user moves one or both sliders 35 connected to different ones of the plates 40, 42 or the clamp 34, causing the clamp 34 to release the tendons 30. In the example of FIGS. 4 and 5, the sliders 35 rotate the plates 40, 42 from the closed or clamped position shown in FIG. 4 to the open position shown in FIG. 5. The sliders 35 are on an exterior of the cap 29, allowing manual operation after the cap 29 is connected to the handle 21. In response to movement of the sliders 35, the clamp 34 releases the anchors 33. After the system is clipped together, the two sliders 35 are pushed apart to open the fan lock and allow motion of the tendons 30.

The actuators 44 and/or clamp 34 may be controlled by a controller. The controller may respond to user input, such as user rotation of knobs or pressing of buttons, to actuate the actuators 44 and/or the clamp 34. The controller interfaces with a user interface for physician control or even teleoperation. Alternatively, the controller responds to programming for automated steering of the catheter without steering input by the user.

The controller is a processor, application specific integrated circuit, integrated circuit, digital signal processor, field programmable gate array, or other control device for controlling the motors of the robotic system. The controller is configured by design, hardware, and/or software to translate and/or rotate the shaft 20 using control from a user interface or input or other controls. The controller is configured to control operation of the actuators 44, thus controlling the translation and the rotation of the catheter 12.

Figure 6:
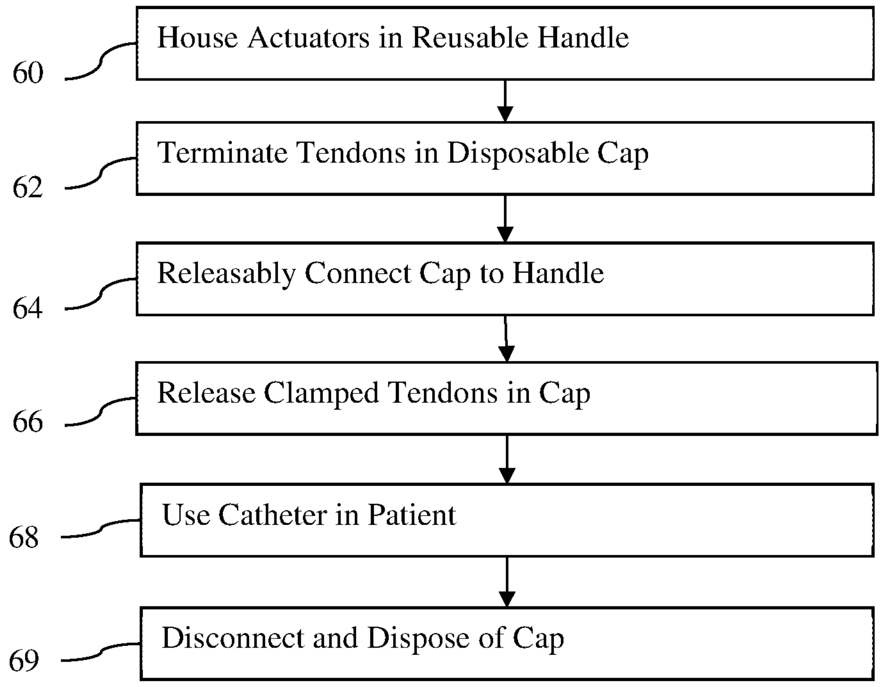
FIG. 6 is a flow chart diagram of one embodiment of a method for robotically operating a catheter.

FIG. 6 is a flow chart diagram of one embodiment of a method for separating a catheter from robotic components. The separation is by design so that separation is provided by having separate handle and cap. Clamping tendons in the cap assists in separation.

The method is implemented by the system and/or robotic system of FIGS. 2-5 or another system. The method uses the ICE catheter and imaging system of FIG. 1 or a different catheter. The method is described below using the catheter 12 of FIG. 1 and the separate components and clamping of FIGS. 2-5. Other robotic systems and/or catheters may be used.

Additional, different, or fewer acts may be provided. For example, acts 60 and 62 are not provided. As another example, act 66 is not provided. In yet another example, acts 68 and 69 are not provided. As yet another example, only one or both of act 64 and act 66 are performed.

The acts are performed in the order shown (numerical or top-to-bottom) or a different order. In the example of FIG. 6, acts 60 and 62 are performed simultaneously, in opposite order, or the order shown.

In act 60, one or more actuators 44 are housed in a handle 21. Rather than connecting actuators 44 separate from the handle 21 through gearing to a knob of the catheter 12, the handle 21 is designed to include the actuators 44 in the handle 21. The actuators 44 are part of the handle 21.

The handle 21 is manufactured as a reusable part. Since the actuators 44, and possibly other electronics, are built into the handle 21, reusing the handle 21 saves cost as compared to disposing of the handle 21 after one use. For re-use, the handle 21 is separate from the catheter 12 as the catheter 12 is used only once or a limited number of times. Thus, the catheter 12 may be thrown out while the handle 21 is used more times or again.

In act 62, one or more tendons 30 terminate in a cap 29. The catheter 12 includes tendons 30 for steering. Since the handle 21 is a separate device to allow for reuse, the tendons 30 terminate in the cap 29 rather than the handle 21.

The tendons 30 are held in place within the cap 29. For example, a clamp 34 holds the tendons 30.

In act 64, a user releasably connects the cap 29 to the handle 21. A snap fit, threaded fit, magnetic fit, or other fitting is used. The cap 29 is positioned against the handle 21, and the fitting engaged to hold the cap 29 to the handle 21. For example, the cap 29 is pressed against the handle 21, twisted to move extensions 38 past the structures 47, and released to lock the extensions 38 to the structures 47 through spring force.

The connection is releasable. The connection may be undone. The connection holds through a threshold amount of force and/or for forces applied in certain directions. For greater force and/or force applied in a specific direction, the cap 29 may be released from the handle 21. For example, the cap 29 is pressed against the handle 21, twisted, and then removed.

In connecting the cap 29 to the handle 21, one or more shafts 45 of the one or more actuators 44 are connected to one or more tendons 30, respectively. The ends of the shafts 45 are configured to connect with the tendons 30, such as anchors 33 at the terminal ends of the tendons 30. Press or snap fit, twist-based thread or engagement, or another connection may be provided. In one embodiment, a magnet fixed to the tendon 30 or to the end of the shaft 45 magnetically links with ferrous metal or another magnet on the other of the end of the shaft 45 or the tendon 30, respectively. Magnetic force connects the tendon 30 to the shaft 45.

In act 66, the clamp 34 releases the tendons 30. As or after the shafts 45 connect with the tendons 30, the tendons 30 are released within the cap 29 by the clamp 34. The release occurs automatically, such as through a mechanism, or occurs manually, such as by a user operating the slides 35. Once the tendons 30 are connected with the shafts 45 for steering operation, then the tendons 30 may be released to allow for steering. Before connection of the cap 29 with the handle 21, the tendons 30 are held in place. After connection, the tendons 30 are released for operation of the catheter 12.

In act 68, the user uses the catheter 12 in a patient. As part of the use, the catheter 12 is steered. Based on a user interface, the user steers the catheter 12. To steer, the tension on the tendons 30 is changed. For example, the user rotates a knob, slides a slider, or presses a button to cause one tendon 30 to apply less pressure and another tendon 30 to apply more pressure, causing the catheter 12 to bend within the patient. The change in pressure is provided by the actuators 44 pushing or pulling the tendons 30 in robotic operation or by the user applied force in manual operation.

Steering may also be provided by rotating the handle 21. The handle 21, as connected to the cap 29, connects with the catheter 12. By rotating the handle 21-cap 29 combination, the catheter 12 rotates about the longitudinal axis of the catheter 12. Similarly, the handle 21 may be used to push or pull the catheter 12 within the patient, altering the point along the cardiac system at which the tip 32 of the catheter 12 is located.

During and/or after steering and/or positioning, the catheter 12 is used. For an intervention catheter, drugs may be injected from the catheter 12 or a tool on the catheter 12 is used (e.g., scissors, needle, ablation electrode, scalpel, or another instrument). For the imaging catheter of FIG. 1, the transducer 16 is used for ultrasound scanning in a field of view 18. Ultrasound imaging is performed with the transducer 16. The user may view the surrounding tissue in different directions by rotating the catheter 12, moving the transduce 16 to a different point, and/or other steering. Changes in bending may alter the field of view to image other anatomy or devices in the patient.

Once the catheterization is complete, the catheter 12 is removed from the patient. For example, the user uses the handle 12-cap 29 combination as connected to pull the catheter 12 out of the patient.

In act 69, the cap 29 is disconnected from the handle 21. The fitting is undone. For example, the cap 29 is pressed against the handle 21, compressing a spring 37. The cap 29 is then rotated relative to the handle 21, moving the extensions 38 away from the structures 47. The cap 29 is then slid from the handle 21.

Once disconnected, the cap 29 and catheter 12 may be discarded. For example, the catheter 12 is a one-time use device. Since the cap 29 connects to the catheter 12 in a fixed manner, the cap 29 is discarded with the catheter 12. The handle 21 may be reused. After any cleaning, the handle 21 may be used again for acts 64-68 with a new cap 29 and catheter 12. The actuators 44 and other electronics in the handle 21 are usable more times than the catheter 12 and cap 29.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A robotic catheter system comprising:

a handle comprising one or more actuators, and a housing cap releasably connectable with the handle, the housing cap having one or more tendons connected to a catheter and a releasable clamp configured to hold the one or more tendons when the housing cap is not connected to the handle, wherein the handle and housing cap are configured so that when the housing cap connects with the handle, the one or more tendons engage with the one or more actuators.

2. The robotic catheter system of claim 1 wherein the one or more actuators comprise one or more linear actuators.

3. The robotic catheter system of claim 1 wherein the one or more tendons terminate at respective one or more anchors, wherein the one or more anchors are releasably connectable to shafts of the one or more actuators, respectively.

4. The robotic catheter system of claim 3 wherein the anchors or ends of shafts comprise magnets such that the anchors are releasably connectable to the ends of the shafts via magnetism.

5. The robotic catheter system of claim 1 wherein the housing cap comprises one or more extensions configured to connect to the handle with a twist motion.

6. The robotic catheter system of claim 5 wherein the housing cap comprises a spring configured to be compressed for connection of the housing cap with the handle, the extensions including hooks to engage the handle where the spring disposes the hooks to stay in place when connected.

7. The robotic catheter system of claim 1 wherein the one or more tendons are connected to one or more anchors, respectively, and wherein the releasable clamp is configured to hold the one or more anchors until the housing cap connects to the handle.

8. The robotic catheter system of claim 1 wherein the releasable clamp comprises a fan lock connected to a slider exposed on an exterior of the housing cap, the fan lock configured to release the one or more tendons in response to movement of the slider relative to the housing cap.

9. A method for separating a catheter from a robotic component, the method comprising:

housing one or more actuators in a handle;

clamping, with a releasable clamp within a cap, a proximal end of one or more tendons within the cap;

connecting the cap to the handle; and releasing the clamping of the one or more tendons after connecting the cap to the handle;

wherein connecting the cap to the handle connects one or more shafts of the one or more actuators to the one or more tendons, respectively.

10. The method of claim 9 wherein connecting comprises pressing the cap to the handle and against a spring force and twisting the cap relative to the handle, the twisting engaging the cap to the handle.

11. A catheter system comprising:

a housing connected with a catheter;

one or more tendons of the catheter extending into the housing;

a releasable clamp in the housing, the releasable clamp configured to clamp the one or more tendons; and a handle releasably connectable with the housing where the handle being connected with the housing also connects shafts of actuators in the handle with the one or more tendons, wherein the releasably clamp is configured to clamp until the one or more tendons are connected to the shafts.

12. The catheter system of claim 11 wherein the one or more tendons terminate at one or more anchors, respectively, and wherein the releasable clamp is configured to clamp the one or more anchors.

13. The catheter system of claim 12 wherein the one or more anchors comprise one or more bushings, respectively, and wherein the releasable clamp is configured to clamp around a part of each of the one or more bushings.

14. The catheter system of claim 11 wherein the releasable clamp is configured to clamp all of the one or more tendons.

15. The catheter system of claim 11 wherein the releasable clamp comprises a fan lock.

16. The catheter system of claim 15 wherein the fan lock comprises two plates, at least one of the plates rotatable in relative to another of the plates where rotation in a first direction clamps terminal ends of the one or more tendons and where rotation in a second direction releases the terminal ends.

17. The catheter system of claim 11 further comprising a slider on an exterior of the housing, the slider connected to the releasable clamp to release the one or more tendons.

* * * * *